United States Patent
An

(10) Patent No.: US 9,963,672 B2
(45) Date of Patent: May 8, 2018

(54) COMPOSITIONS AND METHODS FOR EXTENDING STORAGE TIME OF COMPETENT CELLS AT -20° C

(71) Applicant: New England Biolabs, Inc., Ipswich, MA (US)

(72) Inventor: Lixin An, Danvers, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days. days.

(21) Appl. No.: 15/321,319

(22) PCT Filed: Jul. 15, 2015

(86) PCT No.: PCT/US2015/040508
§ 371 (c)(1),
(2) Date: Dec. 22, 2016

(87) PCT Pub. No.: WO2016/014307
PCT Pub. Date: Jan. 28, 2016

(65) Prior Publication Data
US 2017/0198250 A1   Jul. 13, 2017

Related U.S. Application Data

(60) Provisional application No. 62/041,367, filed on Aug. 25, 2014, provisional application No. 62/026,903, filed on Jul. 21, 2014.

(51) Int. Cl.
*C12N 1/04* (2006.01)
*C12N 1/20* (2006.01)

(52) U.S. Cl.
CPC   *C12N 1/04* (2013.01); *C12N 1/20* (2013.01)

(58) Field of Classification Search
None
See application file for complete search history.

(56) References Cited

FOREIGN PATENT DOCUMENTS

| WO | WO98/35018 | 8/1998 |
| WO | WO02/36745 | 5/2002 |
| WO | WO2004/031363 | 4/2004 |

OTHER PUBLICATIONS

Hanahan, et al., Methods in Enzymology, 204:63-113 (1991).
International Searing Authority, International search report for International Application No. PCT/US2015/040508 dated Sep. 28, 2015.
Ahn, et al., Biotechnology Letters, 26:1593-1594 (2004).

*Primary Examiner* — James S Ketter
(74) *Attorney, Agent, or Firm* — New England Biolabs, Inc; Harriet M. Strimpel

(57) ABSTRACT

Compositions and methods are provided for storing prokaryotic cells including competent prokaryotic cells at −20° C. in a buffer so that the cells are suitable for transformation at 0° C. with a foreign molecule.

7 Claims, 2 Drawing Sheets

COMPOSITIONS AND METHODS FOR EXTENDING STORAGE TIME OF COMPETENT CELLS AT -20° C

CROSS REFERENCE

This application is a § 371 application of International Application No. PCT/US2015/040508 filed Jul. 15, 2015, which claims priority from U.S. Provisional Application No. 62/026,903 filed Jul. 21, 2014 and U.S. Provisional Application No. 62/041,367 filed Aug. 25, 2014 herein incorporated by reference.

BACKGROUND

Competent cells are available for cloning vectors of interest for molecular biology research. A variety of competent cells are provided commercially for various types of laboratory procedures such as routine cloning, protein expression, and library production. Bacterial cells are rendered competent in the presence of high salt and are then washed and resuspended in a high salt solution for storage at -80° C. Storage at -80° C. is at best a costly inconvenience.

SUMMARY

In general, a method is provided that includes removing salts from prokaryotic cells optionally induced to competency by a first salt containing buffer; adding a storage buffer comprising glucose or an oligosaccharide containing glucose; storing cells at -20° C. for a period of time; and adding a salt containing buffer to the cells at a time proximate to transformation of the cells with a foreign molecule.

In one aspect, the foreign molecule is a DNA, an RNA or a protein. In another aspect, the prokaryotic cells are E. coli. In another aspect, the storage buffer further comprises glycerol and may further include DMSO. In one aspect, where glucose or an oligosaccharide is added to the storage buffer, its concentration is within a range of 10 mM-500 mM. In one aspect the period of time may be greater than 5 days.

In general, a composition is provided having stabilized competent bacterial cells in a buffer including a monosaccharide and/or an oligosaccharide such as for example trehalose or sucrose or glucose.

In various aspects, the concentration of the one or more monosaccharides or oligosaccharides may be the range of 50 mM-500 mM. The competent bacterial cells may have a concentration of OD600=2-500.

In general, a method is provided that includes storing a composition described above at about -20° C. for at least 5 days; adding a salt containing buffer to the cells in the composition at a time proximate to transformation of the cells with a foreign molecule; and transforming the cells.

DESCRIPTION OF THE FIGURES

FIG. 1A shows the effect of storage at -20° C. of competent cells (●●●) Competent E. coli cells which were previously stored at -80° C. with substantially diminished activity after being stored at -20° C. for 29 days. At the end of the selected time period, the sample was moved to 0° C. and transformed with pUC19.

(—) Competent E. coli which was made by removing the buffer used to prepare cells at time zero followed by storage of the cells in a novel buffer containing 200 mM trehalose, as well as standard DMSO and glycerol and lacking salt did not lose significant activity after being stored up to 105 days at -20° C.

Figure 1A:
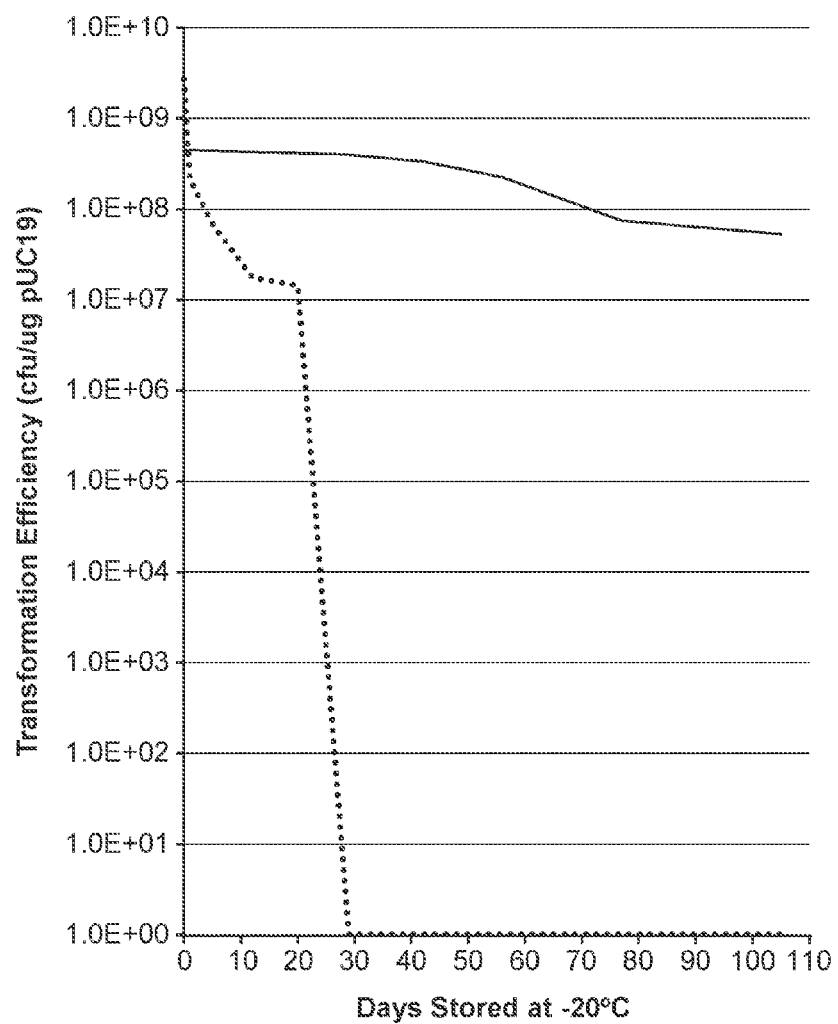
FIG. 1A-1B shows E. coli cells which were stored at 0, 28, 42, 56, 77 and 105 days at -20° C. in a storage buffer containing oligosaccharides and no salt without any significant loss of transformation efficiency compared with a control sample stored at -20° C. in the standard competent cell storage buffer containing salt used for routine storage at -80° C.
Figure 1B:
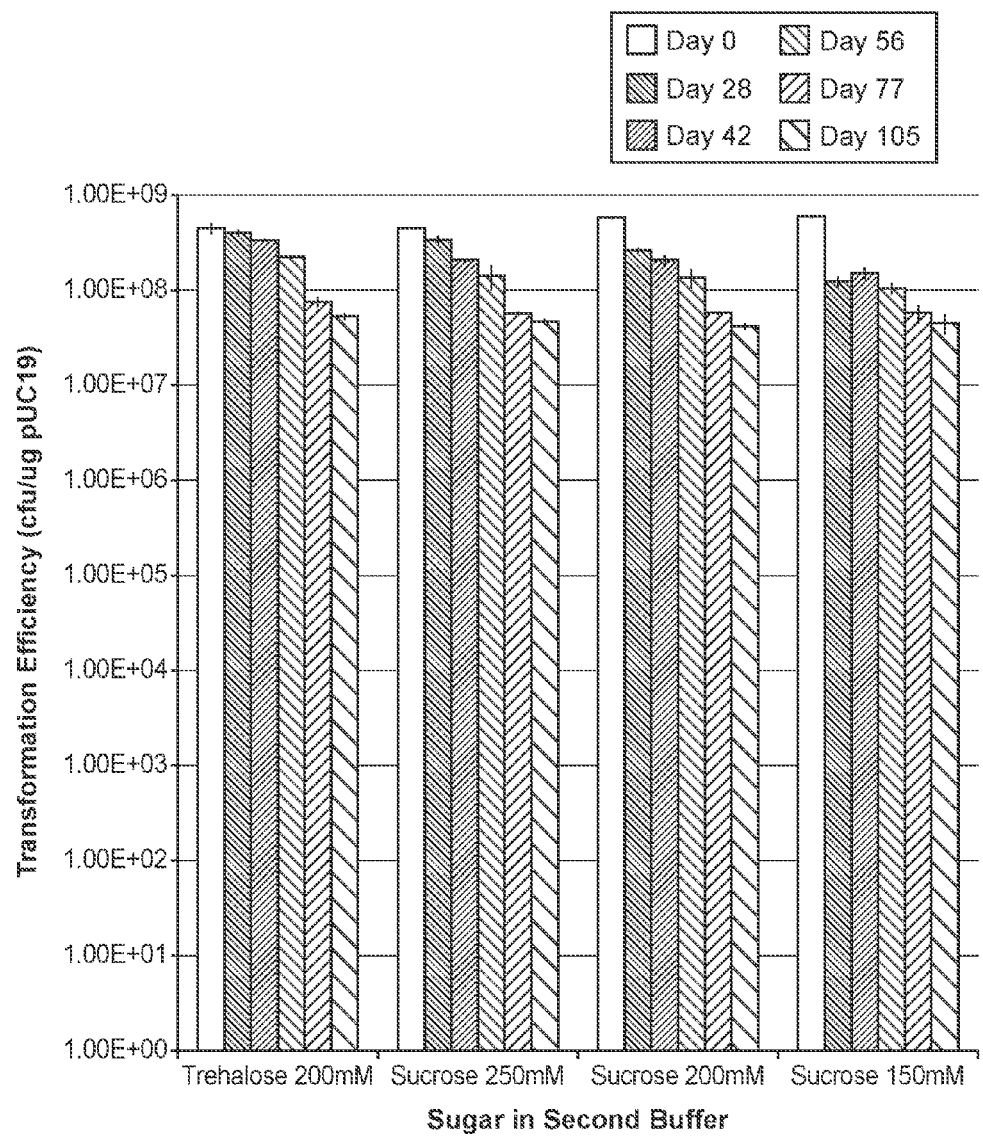

FIG. 1B shows a comparison of competency of E. coli cells which were stored at -20° C. in the novel storage buffer formulation that lacked salt and contained various concentrations of different oligosaccharides in addition to glycerol and DMSO in a standard buffer over various time periods— 1, 28, 42, 56, 77 and 105 days showing remarkable stability.

At the end of the selected time period (0, 28, 42, 56, 77 and 105 days), the sample was moved to 0° C. and transformed with pUC19. The data shows that cells could be stored at -20° C. for as long as 105 days with little or no change in transformation efficiency. Several examples of oligosaccharides were shown to have similar preservative activities. A=trehalose at 200 mM, B=sucrose at 250 mM, C=sucrose at 200 mM and D=sucrose at 150 mM. Data is provided for transformation efficiency after storage.

DESCRIPTION OF EMBODIMENTS

The term "competent" bacteria refers to bacteria having altered cell walls so that DNA can pass through more easily. Generally competent cells are fragile and may lose viability rapidly after thawing from -80° C. so that they are no longer available to take up DNA.

The term "stable" or "stabilized" refers to a preparation of bacterial cells that are capable of retaining a transformation efficiency of at least 1.00E+08 cfu/ug pUC19 when stored for at least 5 days at -20° C.

The term "-20° C." is intended to refer to a temperature suitable for storage that is preferable at -20° C. but may vary according to various factors so that the temperature may represent a range of -15° C. to -30° C.

In embodiments of the invention, bacterial cells can optionally be rendered competent when prepared under standard conditions in a salt containing buffer using standard protocols for preparing competent cells after which the salt is preferably removed (See for example, Hanahan, et al., *Methods in Enzymology*, 204:63 (1991)). The competent cells can then be stored in the novel storage buffer described herein at -20° C. and after thawing can remain competent for an extended period of time when a salt containing buffer is added to the thawed cells. Such competent bacterial cells are suitable for transformation by biological macromolecules such as DNA, RNA and protein. The examples provided herein measure transformation efficiency with pUC19 DNA.

Competent bacterial cells (for example those tested in FIG. 1B), can be washed (for example, with water) to remove salt which may optionally be utilized prior to placing cells at -20° C. in a storage buffer containing glycerol, DMSO and sugars. Glycerol may be used at a concentration of 1%-50%, and DMSO may be used at a concentration of 1%-25%. By way of an example, FIG. 1A shows loss of competency of cells stored in a conventional storage buffer at -20° C. where the conventional storage buffer includes 10% glycerol and 7% DMSO suitable for standard conditions of storage at -80° C. In contrast, FIG.

1B shows sustained levels of competency at −20° C. in the novel storage buffer which contains 20% glycerol, 14% DMSO, one or more sugars and optionally ethylene glycol and/or propylene glycol. In FIG. 1B, the assay for competency included moving the cells to 0° C. and adding an equal volume of a salt buffer to the storage buffer. The cells were then transformed with biological macromolecules.

The sugars in the storage buffer comprise one or more glucose monosaccharides or oligosaccharides comprising glucose and having a size of 2-10 monosaccharides. In one embodiment, the monosaccharide or oligosaccharide in an amount of 10 mM-500 mM, for example, 50 mM-500 mM for example 50 mM-200 mM of the monosaccharide or oligosaccharide was added to cells having a concentration in the range of $OD_{600}$=1-500, for example, $OD_{600}$=2-250, $OD_{600}$=3-100, $OD_{600}$=4-75, or $OD_{600}$=5-50. It should be understood by a person of ordinary skill in the art that a monosaccharide or oligosaccharide for use herein might include something other than glucose such as xylose or ribose. While not intended to be limiting, FIG. 1B shows the advantageous effect of a single concentration of a disaccharide, trehelose that is composed of two alpha glucose units, and sucrose at 3 different concentrations. In addition to the above, ethylene glycol and/or propylene glycol to the storage buffer may be added at concentrations in the range of 0.1 mM-1000 mM.

Storage preferably occurs in the absence of salts of the amount and type used to generate the competent cells.

The storage conditions used herein are suitable for any competent *E. coli* strain including *E. coli* K-12, *E. coli* B, *E. coli* W and *E. coli* C.

Cells stored in the manner described herein were found to be capable of retaining competency for at least 5, 10, 15, 20, 25, 30, 35, 40, 42 days.

What is claimed is:

1. A method comprising:
   preparing competent prokaryotic cells;
   adding an aqueous storage buffer comprising: i. glucose or an oligosaccharide containing glucose; and
   storing the cells in the aqueous storage buffer at a temperature in the range of −15° C. to −30° C. for a period of at least 5 days,
   wherein the competency of the cells does not significantly decrease during storage.

2. A method according to claim 1, wherein the prokaryotic cells are *E. coli*.

3. A method according to claim 1, wherein the storage buffer further comprises glycerol.

4. A method according to claim 1, wherein the storage buffer further comprises DMSO.

5. A method according to claim 1, wherein the glucose or the oligosaccharide comprising glucose is present within a range of 10 mM-500 mM.

6. A method comprising:
   obtaining competent prokaryotic cells in an aqueous storage buffer comprising: glucose or an oligosaccharide containing glucose,
   wherein the cells have been stored in the buffer at a temperature in the range of −15° C. to −30° C. for at least 5 days;
   raising the temperature of the cells in the aqueous storage buffer; and
   after raising the temperature of the cells in the aqueous storage buffer, transforming the cells with a foreign molecule.

7. The method of claim 6, wherein the foreign molecule is a nucleic acid.

* * * * *